(12) United States Patent
Fischer et al.

(10) Patent No.: US 6,440,453 B1
(45) Date of Patent: Aug. 27, 2002

(54) TRANSDERMAL SYSTEMS FOR RELEASE OF 5-$HT_3$ RECEPTOR ANTAGONISTS AND THEIR USE IN ANTI-EMETIC TREATMENT

(75) Inventors: Wilfried Fischer; Axel Stierle, both of Munich (DE)

(73) Assignee: Novosis Pharma AG, Munich (DE)

( * ) Notice: Subject to any disclaimer, the term of this patent is extended or adjusted under 35 U.S.C. 154(b) by 1 day.

(21) Appl. No.: 09/602,003

(22) Filed: Jun. 23, 2000

(30) Foreign Application Priority Data

Jun. 25, 1999 (DE) .......................................... 199 29 197

(51) Int. Cl.[7] .......................... A61F 13/00; A61F 13/02
(52) U.S. Cl. ........................ 424/449; 424/448; 424/443
(58) Field of Search ................................. 424/449, 448, 424/443

(56) References Cited

U.S. PATENT DOCUMENTS

| | | | | |
|---|---|---|---|---|
| 5,254,346 A | * | 10/1993 | Tucker et al. | |
| 5,656,286 A | * | 8/1997 | Miranda et al. | |
| 5,989,586 A | * | 11/1999 | Hsu et al. | |
| 6,228,864 B1 | * | 5/2001 | Smith et al. | |

* cited by examiner

Primary Examiner—Thurman K. Page
Assistant Examiner—Isis Ghali
(74) Attorney, Agent, or Firm—Frommer Lawrence & Haug LLP; Ronald R. Santucci

(57) ABSTRACT

This invention refers to a transdermal system for release of 5-$HT_3$ receptor antagonists which is characterized in that it contains a composition of a 5-$HT_3$ receptor antagonist as an active agent, tea tree oil, a water-miscible solvent and water.

21 Claims, 1 Drawing Sheet

TRANSDERMAL SYSTEMS FOR RELEASE OF 5-HT₃ RECEPTOR ANTAGONISTS AND THEIR USE IN ANTI-EMETIC TREATMENT

INTRODUCTION AND STATE OF THE ART

The therapy of tumor illnesses with anti-tumor drugs, e.g., among others with cisplatin derivatives, is often accompanied by strong sensations of nausea and the tumors themselves can also cause nausea or emesis. At present, the modern treatment form of strong emesis involves antagonists of serotonin (=5-hydroxytryptamine a=5-HT) receptors of the 5-HT$_3$ type.

Ondansetron hydrochloride can be mentioned as an example of a specific antagonist for both the chemoreceptors as well as the receptors of the gastrointestinal tract. Further 5-HT$_3$ antagonists are granisetron hydrochloride, azasetron hydrochloride, rarnosetron hydrochloride and their bases.

Approximately 1 hour after oral administration and 6 to 20 minutes after an intravenous administration of ondansetron hydrochloride, peak concentrations are present in the plasma. The average elimination half-life for healthy test persons is 3.5 hours and is increased to approximately 7.9 hours in older patients.

Ondansetron is reliable in treating nausea and emesis in patients who have to undergo treatment with anti-tumor drugs such as cisplatin derivatives. As side effects headaches, diarrhea, and temporary abnormalities in liver function tests occur. The dose of ondansetron as a prophylactic measure against vomiting induced by anti-tumor drugs is generally 0.15 mg/kg i.v. three times a day every 4 hours.

From a chemical point of view, ondansetron is the dihydrate of (±)-1,2,3,9-tetrahydro-9-methy-3-[(2-methyl-1H-imidazole-1-yl)methyl]-4H-carbazol-4-one monohydrochloride.

The molecular formula is $C_{18}H_{19}N_3O \cdot HCl \cdot 2H_2O$, which corresponds to a molecular weight of 365.9 g.

Ondansetron is metabolized to a large extent in humans but only approximately 5% of a radioactively marked dose can be found in urine. The primary pathway of metabolism is the hydroxylation at the indole ring followed by glucuronization or sulfation.

The pharmacokinetic data summarized in the table were determined with healthy test persons after a single intravenous administration of a dose of 0.15 mg/kg i.v.

| age group (years) | peak concentration in plasma (ng/ml) | average half-life (h) | plasma clearance (l/h/kg) |
| --- | --- | --- | --- |
| 19–40 | 11,102 | 3.5 | 0.38 |
| 61–74 | 12,106 | 4.7 | 0.32 |
| ≧75 | 11,170 | 5.5 | 0.26 |

The binding of ondansetron to plasma protein is approximately 70% to 76% and this was measured in vitro in the pharmacologically important concentration range of 10 to 500 nglml.

Ondansetron is absorbed wee after oral administration and undergoes a first-pass-metabolism via the liver passage. The relative bioavailability after administration of 8 mg tablets to healthy test persons is approximately 56%.

Since the administration of 5-HT$_3$ antagonists is conducted by parenteral infusion before administration of anti-tumor drugs and since bioavailability is only approximately 50% (e. g., for ondansetron) after oral administration and since long-term administration of the substances is required, a more agreeable and more reliable method of application must be provided for patients on whom injections and infusions, especially during therapy with anti-tumor drugs, put a heavy strain.

The transdermal administration of highly effective substances, such as, hormones, strong analgesics, nitrates, etc., has been known for several years.

Ondansetron is commercially available under the trade name Zofran® in a form suitable for injections or in the form of tablets for oral administration. At present, a form suitable for transdermal application does not exist.

WO 9825592, based on JP 96-346460, describes transdermal systems, which consist of at least three layers: (A) a "backing layer", which is impermeable for the active agent, (B) a layer which serves as a reservoir of the active agent and which contains a serotonin receptor antagonist, and (C) a layer which controls release of the active agent. This layer consists of a pressure-sensitive adhesive which controls release of the active agent.

WO 9407468, based on U.S. 92-956635, assigned to Cygnus Therapeutic Systems, USA, describes a "two-phase matrix for sustained-release transdermal pharmaceuticals" as a transdermal system. The gist of this invention is that a second phase, which consists of hydrated inorganic silicate in the absorbed water phase of which a water-soluble active agent is dissolved, is dispersed in a hydrophobic continuous polymer, which optionally contains a hydrophobic solvent which is effective in enhancing permeation. For example, a matrix, which consists of 4 % (R)-(−)-N-(1-methyl-4-(3-methylbenzyl)hexahydro-1H-1,4-diazepin-6-yl)-1H-indazole-3-carboxamided.2HCl, 10% propylene glycol monolaureate, 20% propylene glycol, 20% water, 7% calcium silicate, 2% Pluronic L-121 and dimethyl siloxane adhesive ad 100%, can be prepared by applying a solution of the above composition at a thickness of 250 $\mu$m on a polyester film, drying and covering with a polyester film. The flow of the active agent through the human epidermis in a diffusion cell was 17.1 $\mu$m/cm$^2$/h in vitro, compared to 0.8 $\mu$g/cm$^2$/h for an adhesive matrix of styrene-butadiene copolymer which was used as a comparison.

At present, transdermal systems (which are to be understood in a broader sense, i.e. systems which in general are suitable for absorption through the skin) for 5-HT$_3$ receptor antagonists do not exist.

The object of the invention is, therefore, to provide a transdermal system for release of 5-HT$_3$ receptor antagonists which functions reliably and is kind to the skin and with which the disadvantages connected to the state of the art can be avoided.

This object is achieved according to the invention by a transdermal system for release of 5-HT$_3$ receptor antagonists having the features recited in claim 1.

Further advantageous embodiments are subject matter of the dependent claims.

The invention also describes the use of the transdermal systems for release of 5-HT$_3$ receptor antagonists according to the invention in anti-emetic treatment (i.e. for the treatment of nausea and emesis).

SHORT DESCRIPTION OF THE FIGURES

DETAILED DESCRIPTION OF THE INVENTION

The transdermal system according to the invention provides improved permeation of ondansetron through the skin by using a combination of tea tree oil, a water-miscible solvent and water as a resorption or permeation enhancer, respectively.

Surprisingly, in experiments for improving resorption, it was found that alcohol which is usually employed as a resorption enhancer, e. g., for sex hormones and analgesics such as fentanyl, does not provide a sufficient improvement in resorption for ondansetron. It was further surprising that the ionic hydrochloride in combination with the described solvent mixture permeates better than ondansetron in the form of the free, non-ionic base.

Figure 1:
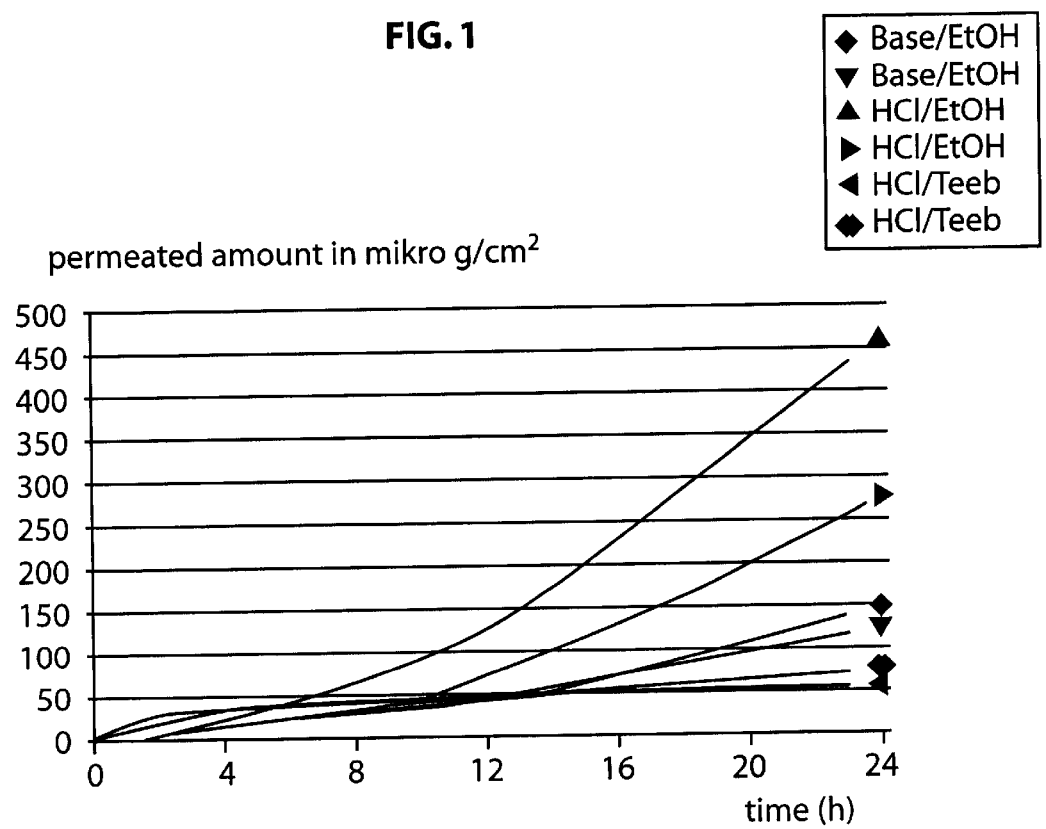
FIG. 1 shows the in vitro skin permeation of ondansetron base and ondansetron hydrochloride through the skin of a nude mouse. All employed solutions are saturated.

The extent of permeation of ondansetron (in form of the free base and the hydrochloride, respectively) through the skin, in vitro, using saturated solutions of ondansetron. HCl in ethanol, saturated solutions of the free base in ethanol and saturated solutions of the hydrochloride in tea tree oil is shown in FIG. 1. Saturated solutions were used to achieve the respective maximal thermodynamic activities.

FIG. 1 shows that best permeation through the skin is achieved when using the hydrochloride in ethanol. Tea tree oil alone results in insufficient permeation, while the base in ethanol only leads to slightly improved results.

Figure 2:
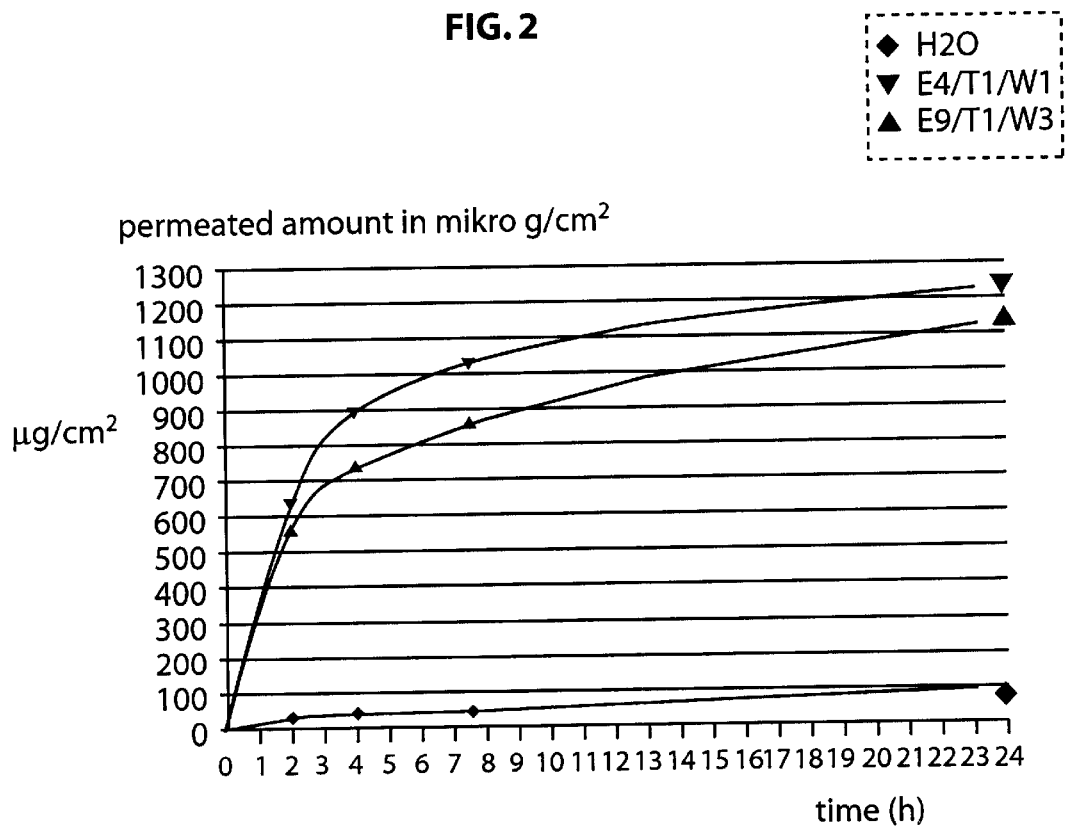
FIG. 2 shows the in vitro skin permeation of ondansetron hydrochloride through the skin of a nude mouse. The given values are average values which were obtained with saturated solutions.

If, as shown in FIG. 2, a saturated aqueous solution of ondansetron hydrochloride is applied to the skin of a nude mouse, the results do not differ from those which were obtained using pure tea tree oil.

If, however, a solution of ondansetron hydrochloride in a mixture or a composition of ethanol, tea tree oil and water is applied to the skin, the permeation behavior of the active agent is changed in an unexpected manner. In the first 4 to 5 hours an extremely strong increase of the flow of the active agent is observed. Then the permeation curve flattens probably due to the reduction of the concentration of active agent in the donor compartment. After 24 hours approximately 1.2 mg ondansetron hydrochloride per $cm^2$ have permeated, i.e. approximately 12 times the amount which diffuses out of a saturated aqueous solution through the skin of the mouse.

The solutions according tot invention having 5-$HT_3$ antagonists as an active agent can be incorporated into gel-, ointment- or creme-type carrier systems (transdermal systems in a broader sense) and can be used in flat transdermal systems (transdermal systems in a more restricted sense), i.e. so-called "transdermal therapeutic systems (TTS)", e. g., plasters with active agents, or in reservoir systems (reservoir-TTS).

Preferred embodiments are transdermal systems in a more restricted sense, especially those having a reservoir. These transdermal systems consist of a covering or cover film (backing foil) which is impermeable for the active agent and which consists of polyester, polpropylene, polyethylene or the like. The backing foil forms a reservoir in the form of a pouch together with a microporous membrane, whereby the membrane can control the passage of the active agent or does not exert any control on diffusion. The solutions of the active agent according to the invention are filled into the reservoir in the form of a pouch. After filling, the backing foil is sealed or adhered to the membrane and then, optionally, a layer of adhesive is applied which affixes the transdermal system to the skin. Instead of a layer of Adhesive a ring of adhesive can also be applied so that the membrane lies directly on the skin.

In the following, the invention is explained with the help of the examples.

EXAMPLES

Example 1

Solution, of the Active Agent

Ondansetron hydrochloride is dissolved to the limit of saturation in a mixture of 1 part water, 1 part tea tree oil and 4 parts ethanol.

Reservoir TTS

Using a suitable thermal sealing apparatus a polyester film having a heat-sealable coating, a thickness of 19 μm and a circular area of 30 $cm^2$ is sealed at its edges to a cellulose acetate membrane having a pore size of approximately 0.1 μm in a way that a fill opening remains, through which 1 ml of the above solution of active agent is filled into the formed pouch. Then, the fill opening is also sealed. A circular area of 20 $cm^2$ results; the solution of active agent can diffuse out through the membrane side thereof For affixing to the skin, a ring of adhesive is mounted onto the edge of the reservoir of liquid, whereby the ring of adhesive consists of a pressure-sensitive adhesive, e.g., Duro-Tak 386-2287 (National, Zutphen, the Netherlands), on a 19 μm thick polyester film, e. g., Hostaphan MN 19 (Mitsubishi Foils, Frankfurt, Germany). The complete system is mounted on a siliconized polyester film or siliconized paper (release liner). Th release liner is removed and discarded before application to the skin.

Example 2

Solution of the Active Agent

Ondansetron hydrochloride is dissolved to the limit of saturation in a mixture of 3 parts water, 1 part tea tree oil and 9 parts ethanol.

Reservoir TTS

A siliconized polyester film is uniformly coated with a solution of a pressure-sensitive acrylate adhesive (e. g., ETA 1, Adhesive Research, Glen Rock, USA) by a blade, followed by vaporizing the solvent so that a uniform layer having a thickness of 40 μm is formed. The layer of adhesive is covered with a polypropylene membrane having an average pore size of 0.2 μm. Then using a suitable thermal sealing apparatus a circular polyester film having a heat-sealable coating, a thickness of 19 μm and an area of 20 $cm^2$ sealed to the membrane side of the above laminate at its edge in a way that a fill opening remains.

0.5 ml of the above solution of active agent is filled into the formed pouch. Then, the fill opening is also sealed. A circular area of 10 $cm^2$ is formed. After removing the siliconized polyester film the transdermal system can be adhered to the skin by the layer of adhesive. The delivery of the active agent to the body takes place through the microporous membrane and the adjacent layer of adhesive.

What is claimed is:

1. Transdermal system for release of 5-$HT_3$ receptor antagonists comprising a composition comprising a 5-$HT_3$ receptor antagonist as an active agent, tea tree oil, ethand and water.

2. Transdermal system according to claim 1, wherein the 5-$HT_3$ receptor antagonist is selected from the group consisting of ondansetron hydrochloride, granisetron hydrochloride, azasetron hydrochloride, ramosetron hydrochloride or a base thereof.

3. Transdernal system according to claim 1, wherein the composition comprises 1 part water, 1 part tea tree oil and 4 parts ethanol in which ondansetron hydrochloride is dissolved to the limit of saturation.

4. Transdermal system according to claim 1, wherein the composition comprises 3 parts water, 1 part tea tree oil and 9 parts ethanol in which ondansetron dydrochloride is dissolved to the limit of saturation.

5. Transdermal system according to claim 1, wherein the composition further comprises a pharmaceutically acceptable carrier which is suitable for preparing gels, ointments or cremes.

6. Transdermal system according to claim 1, wherein the composition is contained in a layer of a flat self-adhering plaster which has a multilayer construction and affixes the transdermal system to the skin.

7. Transdermal system according to claim 6, wherein a cover, a layer of adhesive and, on the side opposite the cover, a removable carrier which temporarily covers the layer of adhesive are provided in addition to the layer containing the composition of active agent.

8. Transdermnal system according to claim 7, wherein the composition of active agent is contained in the layer of adhesive.

9. Transdermal system according to claim 7, wherein the cover consists of a film of plastic, woven fabric or non-woven fabric.

10. Transdermal system according to claim 7, wherein the carrier consists of a film of plastic, paper or a laminate thereof.

11. Transdermal system according to claim 1, wherein the composition is contained in a reservoir of a flat self-adhering plaster, the reservoir being formed of a microporous membrane which is permeable for the active agent.

12. Transdermal system according to claim 11, wherein the membrane which is permeable for the active agent consists of cellulose acetate, polyester or polypropylene.

13. Transdermal system according to claim 11, wherein the membrane which is permeable for the active agent has a pore size of 0.1 $\mu$m to 0.2 $\mu$m.

14. Transdermal system according to claim 11, wherein in addition to the reservoir containing the composition of active agent, a cover which is impermeable for the active agent, a ring of adhesive which is on the side of the reservoir which is opposite the cover, are provided.

15. Transdermal system according to claim 14, wherein the cover consists of a film of plastic.

16. Transdermal system according to claim 14, wherein the carrier consists of a siliconized film of plastic or siliconized paper.

17. Transdermal system according to claim 15, wherein the film of a plastic is polyester film, polyethylene film or polypropylene film.

18. A method of treating nausea and/or emesis using a transdermal system comprising a composition comprising a 5-$HT_3$ receptor antagonist as an active agent, tea tree oil, ethanol and water is applied to the skin and delivers the active agent to the body.

19. The method according to claim 18, wherein the 5-$HT_3$ receptor antagonist is selected from the group consisting of ondansetron hydrochloride, granisetron hydrochloride, azasetron hydrochloride, ramosetron hydrochloride or a base thereof.

20. The method according to claim 18, wherein the composition comprises 1 part water, 1 part tea tree oil and 4 parts ethanol in which ondansetron hydrochloride is dissolved to the limit of Saturation.

21. The method according to claim 18, wherein the composition comprises 3 parts water, 1 part tea tree oil and 9 parts ethanol in which ondansetron dydrochloride is dissolved to the limit of saturation.

* * * * *